United States Patent [19]

Lamar et al.

[11] Patent Number: 5,476,788
[45] Date of Patent: Dec. 19, 1995

[54] SOLID PHASE BIOREMEDIATION METHODS USING LIGNIN-DEGRADING FUNGI

[75] Inventors: Richard T. Lamar; Diane M. Dietrich, both of Madison, Wis.; John A. Glaser, Cincinnati, Ohio

[73] Assignees: The United States of America as represented by the Secretary of Agriculture; The United States of America as represented by the Administrator of the EPA, both of Washington, D.C.

[21] Appl. No.: 364,023

[22] Filed: Dec. 23, 1994

Related U.S. Application Data

[63] Continuation of Ser. No. 74,643, Jun. 10, 1993, abandoned.

[51] Int. Cl.[6] .............................. C12S 12/00; B09B 3/00; C12N 1/22; C12N 1/14
[52] U.S. Cl. ..................... 435/262.5; 435/262; 435/252; 435/254.1; 405/264
[58] Field of Search ................................. 435/262.5, 156, 435/262, 252, 254, 277, 264, 254.1; 405/264

[56] References Cited

U.S. PATENT DOCUMENTS

4,891,320  1/1990  Aust et al. .............................. 435/262

FOREIGN PATENT DOCUMENTS

0192237  2/1985  European Pat. Off. .
3731816  9/1987  Germany .

OTHER PUBLICATIONS

Lamar, R. T., "Biodegradation of PCP–Treated Ammunition Boxes Using White–Rot Fungi." Sep. 1991 NTIS Abstract 92(03):334.
Bumpus et al. "Biological tretment of hazardous wastes by *Phanerochaeta chrysosperium.*" 1989. CABA Abstract 91:24540.
Lamar et al. "Use of Lignin–degrading fungi in the disposal of PCP treated wood." 1992. Biosis Abstract 92:409260.
Lamar et al. "Use of lignin–degrading fungi in the disposal of PCP–treated Wood". *J. of Industrial Microbiology.* vol. 9 No. 3–4 (1992) pp. 181–191.
Bumpus, et. al. "Oxidation of Persistent Environmental Pollutants by White Rot Fungus," Science 288, pp. 1434–1436 (1985).
Bumpus and Aust, "Biodegradation of DTT by the White Rot Fungus . . . ," App. & Env. Microbio. 53, pp. 2001–2007 (1987).
Bumpus and Aust, "Biodegradation of Chlorinated Organic Compounds . . . ," Solving Hazardous Waste Problems, ACS Sypmposium Ser., pp. 340–349 (1987).
Eaton et. al., "Method Obtains Fungal Reduction of the Color of Extraction–Stage Kraft Bleach Effluents," TAPPI 65(6), pp. 89–92 (1982).
Fenn and Kirk, "Relationship of Nitrogen to the Onset and Suppression of . . . ," Arch. Microbiol. 130, pp. 59–65 (1981).
Field et. al., "Biodegradaion of Polycyclic Aromatic Hydrocarbons by New Isolates of White Rot Fungi," App. & Env. Microb. 58(7), pp. 2219–2226 (1992).
George and Neufeld, "Degradation of Flourene in Soil by Fungus . . . " Biotechnol. Bioeng. 33, pp. 1306–1310 (1989).
Haemmerli et. al., "Oxidation of Benzyl(a)pyrene by Extracellular Ligninases . . . ," J. Biol. Chem. 261, pp. 6900–6903 (May 1986).

(List continued on next page.)

*Primary Examiner*—William H. Beisner
*Assistant Examiner*—T. J. Reardon
*Attorney, Agent, or Firm*—Janet I. Stockhausen; M. Howard Silverstein; John D. Fado

[57] ABSTRACT

A solid-phase bioremediation method utilizing naturally occurring lignin-degrading fungi. The method includes inoculating a field-contaminated, nonsterile soil or wood having a halogenated hydrocarbon contaminant with an inoculum containing one or more lignin-degrading fungi and a lignocellulosic substrate, and degrading the contaminant to less toxic degradation products.

13 Claims, 4 Drawing Sheets

OTHER PUBLICATIONS

Hammel, "Organopollutant Degradation by Lignolytic Fungi," Enz. Microb. Techonol. 11, pp. 776–777 (1989).

Hammel and Tardone, "The Oxicative 4–Dechlorination of Polychlorinated Phenols . . . ," Biochem. 27(17), pp. 6563–6568 (1988).

Huynh et. al., "Dechlorination of Chloro–Organics by a White–Rot Fungus," TAPPI 68(7), pp. 98–102 (1985).

Kohler et. al., "Extracellular Ligninase of *Phanerochaete chrysosporium* Bursdall . . . ," App. Microb. Biotech. 29, pp. 618–620 (1988).

Lamar et. al., "Fate of Pentachlorophenol (PCP) in Sterile Soils . . . ," Soil Biol. Biochem. 22(4), pp. 433–440 (1990).

Lamar et. al., "In Situ Depletion of Pentachlorophenol from Contaminated Soil . . . ," App. and Env. Microbio. 56(10), pp. 3093–3100 (1990).

Lamar et. al., "Sentsitivity to and Degradation of Pentachlorophenol . . . ," App. and Env. Microbio. 56(11), pp. 3519–3526 (1991).

Leatham et. al., "Degradation of Phenolic Compounds and Ring Cleavage of Catechol 1 1 1," App. and Env. Microbio. 46(1), pp. 191–197 (1983).

Ryan, et. al., "Biodegradation of 2,4, 5–Trichlorophenoxyacetic Acid in Liquid Culture . . . ," App. Microbio. Biotechnol. 31, pp. 302–307 (1989).

Mileski et. al., "Biodegradation of Pentachlorophenol by the White Rot Fungus . . . ," App. & Env. Microbio. 54(12), pp. 2885–2889 (1988).

Sanglard et. al., "Role of Extracellular Ligninases in Biodegradation of Benzy(a)pyrene . . . ," Enz. Microb. Technol. 8, pp. 209–212 (1986).

Hammel et al. "Oxidation of Polycyclic Aromatic Hydrocarbons and Dibenzo(p)dioxins by *Phanerochaete chrysosporium* Ligninase", *The Journal of Biological Chemistry*, vol. 261, No. 36, pp. 16948–52 (1986).

Unterman, "Bacterial Treatment of PCB–Contaminated Soils," Proceeding of Hazardous Materials Control Research Institute *Hazardous Waste Treatment by Genetically Engineered or Adapted Organisms*, pp. 17–18, Nov. 30–De. 2, 1988, Washington, D.C. (This is resubmitted reference 20 from IDS filed Jun. 10, 1993.)

Lamar, R. T., "Biodegradation of PCP–Treated Ammunition Boxes Using White–Rot Fungi," U.S. Army Corps of Engineers, Toxic and Hazardous Materials Agency Report No. CETHA–TE–TR–91029 Final Report (cover page through end filming page) (31 pages), Sep. 1991. (This is the full report which is associated with the LAMAR R abstract reference from the IDS filed Jun. 10, 1993.)

Lamar, R. T. and Scholze, R. J., "White–Rot Fungi Biodegradation of PCP–Treated Ammunition Boxes," Proceedings of R&D 92 National research & development conference on the control of hazardous materials; 1992 Feb. 4–6; San Francisco, Calif. Greenbelt, Md. Hazardous Materials Control Resources Institute; 1992, pp. 89–94.

- ■ 10% P. CHRYSOSPORIUM
- ● 5% P. CHRYSOSPORIUM
- □ 10% P. SORIDA
- ▲ 5% P. CHRYSOSPORIUM AND 5% T. HIRSUTA

- ■ 10% P. CHRYSOSPORIUM
- □ 13% P. CHRYSOSPORIUM
- ▲ 10% P. CHRYSOSPORIUM DAY 0 FOLLOWED BY 3% DAY 14
- ● 10% T. HIRSUTA

- STERILE HARDWOOD
- NONSTERILE HARDWOOD
- STERILE SOFTWOOD
- NONSTERILE SOFTWOOD

- STERILE HARDWOOD
- NONSTERILE HARDWOOD
- STERILE SOFTWOOD
- NONSTERILE SOFTWOOD

5,476,788

SOLID PHASE BIOREMEDIATION METHODS USING LIGNIN-DEGRADING FUNGI

This is a "continuation" of application Ser. No. 08/074,643 filed Jun. 10, 1993, now abandoned.

TECHNICAL FIELD

This invention relates to the fields of mycology, catabolism of organic substrates, and environmental cleanup. More specifically, the invention involves a method for the bioremediation utilizing lignin-degrading fungal strains acting on solid materials, such as soils, sludge, sediments, and debris (e.g., woods), that are contaminated with halogenated hydrocarbons, particularly with the wood preservative pentachlorophenol.

BACKGROUND OF THE INVENTION

Contamination of soils and ground water with toxic, environmentally persistent chemicals is a serious, ongoing problem. Toxic, environmentally persistent chemicals are those that are resistant to degradation in the natural environment. As such, these chemicals pose a multifaceted problem in that as they persist and accumulate in the environment, their toxicity, including in many instances, proven carcinogenicity, presents substantial health risks to both animals and human beings. The medical literature is full of data on the adverse health effects caused by human exposure to these chemicals.

The scope of this problem can be appreciated when one considers that there are thousands of toxic waste sites in this country where large quantities of these chemicals either have been dumped directly into the soil or have leaked out of storage tanks. The disposal of contaminated materials, e.g., storage containers, manufacturing equipment, and chemically treated materials such as lumber, presents an additional problem.

The types of chemicals that fit the classification of a toxic, environmentally persistent pollutant, and therefore contribute to this problem, are numerous. One such type is the halogenated aromatic compounds (HAC's). HAC's are further categorized into those whose molecular structure has a single aromatic ring and those whose structure contain two or more. The HAC's that contain a single ring include pentachlorophenol (PCP). PCP has been used extensively as a wood preservative. The HAC's containing two or more rings include the pesticide, DDT, and polychlorinated biphenyls and polybrominated biphenyls that have been used extensively in manufacturing.

The prior art is replete with laboratory data on methods for the degradation of hazardous chemicals, generally, and specifically, of HAC's. The difficulty with many of these methods is that while they may be successful in controlled laboratory or controlled field conditions, they often lack effectiveness or practicality in large scale field conditions, i.e., they are less than successful when tried with "field-contaminated" materials. As used herein, the term "field-contaminated" is meant to refer to a solid material, i.e., soil or wood, that has been contaminated through use or accident as compared to laboratory samples that are artificially contaminated, particularly under controlled laboratory conditions. In the case of wood products, "field-contaminated" also is meant to refer to a wood that has been contaminated in the field, a wood that has been intentionally treated for use in commerce, or a wood that is a contaminated by-product of industrial treatment. An example of a wood which has been intentionally treated for use in commerce is wood products which have been treated with a material that contains hazardous chemicals, such as a wood preservative.

Treatment strategies that have been suggested or tried include incineration of the waste, removal and isolation of the contaminated materials, and degradation of the pollutant by bacteria. All of these strategies suffer from serious deficiencies. Incineration is extremely expensive due to the energy requirements and the necessity of hauling the contaminated material to remote locations, as well as impractical due to the large quantities of waste that need to be processed. Removal and isolation of the contaminated material is also expensive and does nothing to effect a long term solution. Degradation of the chemicals by bacteria has proven less than ideal due to the bacteria's specificity for particular chemicals and sensitivity to the toxic chemicals and environmental conditions.

Another potential strategy that has been the subject of experimental research in the past decade is the use of a class of wood degrading fungi, known as lignin-degrading fungi, to degrade HAC's. In the early 1980's, it was reported that the fungus *Phanerochaete chrysosporium* (*P. chrysosporium*) could degrade chlorinated organics in the effluent of a kraft pulp mill (Eaton et al., *TAPPI*, vol. 65 (1982) pp. 89–92; Huynh et al., *TAPPI*, vol. 68 (1985) pp. 98–102). At about this same time, other researchers isolated and characterized the enzymes responsible for the lignin degrading ability of these fungi. These isolated enzymes, termed lignin peroxidases or ligninases, were found to oxidize a wide variety of compounds in addition to lignin. Such compounds include polycyclic aromatic hydrocarbons (Hammel et al., *J. Biol. Chem.*, vol. 261 (1986) pp. 16948–16952; Sanglard et al., *Enzyme and Microbial Tech.*, vol. 8 (1986) pp. 209–212), dibenzo(p)dioxins (Hammel et al., *J. Biol. Chem.*, vol. 261 (1986) pp. 16948–16952; Haemmerli et al., *J. Biol. Chem.*, vol. 261 (1986) pp. 6900–6903), and polychlorinated phenols (Hammel and Tardone, *Biochem.*, vol. 27 (1988) pp. 6563–6568).

It has since been reported that under controlled laboratory conditions, cultures of *P. chrysosporium* can also effectively degrade HAC's. In particular, Bumpus et al. have extensively studied the degradation of the multi-ring halogenated aromatics. They have shown that small cultures of *P. chrysosporium* grown in the laboratory in a low nitrogen-containing growth medium at approximately 37° C. will degrade DDT, 2,4,5,2',4',5'-hexachloro-biphenyl, 2,3,7,8-tetra-chlorodibenzo-p-dioxin, and lindane (see, Bumpus et al., *Science*, vol. 228 (1985) pp. 1434–1436; Bumpus and Aust, *Applied and Environmental Microbiology*, vol. 53 (1987) pp. 2001–2007; Aust and Bumpus, U.S. Pat. No. 4,891,320). Similar studies have analyzed the ability of *P. chrysosporium* to degrade PCP in controlled small cultures (Mileski et al., *Applied and Environmental Microbiology*, vol. 54 (1988) pp. 2885–2889).

Far fewer studies have attempted to more closely approximate conditions that are present at contaminated field sites or investigate the relative efficacies of the many other species of fungi of the lignin-degrading class. Several studies have reported that *P. chrysosporium* can degrade 2,4,5-trichlorophenoxyacetic acid (Ryan et al., *Appl. Microbiol, Biotechnol.*, vol. 31 (1989) pp. 302–307), fluorene (George and Neufeld, *Biotechnol. Bioeng.*, vol. 33 (1989) pp. 1306–1310), and PCP (Lamar et al., *Soil Biol. Biochem.*, vol. 22 (1990) pp. 433–440) in chemically spiked sterile soil in laboratory culture. This latter study also reported that the ability of *P. chrysosporium* to degrade the PCP varied depending on the soil type; the fungi exhibited the highest rate of transformation of the PCP in Marshan soil (sandy loam) and the lowest in Batavia soil (silty clay loam).

Lamar et al., *Appl. Environ. Microbiol.*, vol. 56 (1990) pp.3519–3526, also tested seven species of lignin-degrading fungi in laboratory cultures. They reported significant differences between the species in both the rate and extent of degradation of the PCP. Most recently, in a preliminary field study in 1 $m^2$ plots of soil contaminated exclusively with PCP, the PCP degrading abilities of *P. chrysosporium* and *Phanerochaete sordida* (*P. sordida*) were compared (Lamar et al., *Appl. Environ. Microbiol.*, vol. 56 (1990) pp. 3093–3100). The results showed that in the very alkaline soil (pH approximately 9.6) that had been tilled prior to initiation of the study to allow evaporation of mineral spirits, sterilized, and supplemented with peat moss, both fungi efficiently degraded the PCP over a 45 day period.

Although these laboratory and preliminary field study data are useful in defining a promising technology for the degradation of HAC's, such a technology is useless if it will not work effectively at the large scale needed to clean up the vast quantities of soils and materials contaminated with HAC's. As noted previously, many technologies that were thought to hold great promise for solving a problem did not prove effective when put to a large scale test. One such example was the technology of degradation of the chemical PCB's with certain genetically engineered or adapted bacteria. Results showed that under controlled laboratory conditions, successful degradation was effected. However, when field trials were conducted, the bacteria were found to be too sensitive to the varying environmental conditions for effective use. (R. Unterman, "Bacterial Treatment of PCB-Contaminated Soils," *Hazardous Waste Treatment by Genetically Engineered or Adapted Organisms*, p. 17, Nov. 30–Dec. 2, 1988, Washington, D.C.)

The problems that are encountered when scaling up a technology are numerous. In large scale use, the parameters controlled in the laboratory are uncontrolled. For example, in the laboratory, parameters such as the temperature, humidity, concentration and distribution of the pollutant chemical, purity of the chemical, oxygen ($O_2$) content, pH, and organics/nutrient content of the cultures can be controlled. However, in large scale use, the temperature and humidity will constantly fluctuate. The concentration and distribution of the pollutant chemical will vary in different areas of the contaminated site. The site will be contaminated with other chemicals, The $O_2$ content will depend on such things as water content, the particle size of the soil or contaminated material, and how tightly it is packed. The pH and organics/nutrient content will depend in part on the geology and nature of the dump site.

Compounding these problems are unknowns in terms of what effect the total environment will have on fungi physiology. The environment as a whole (including the parameters listed above as well as others) affects not only the growth rate of the fungi, but also the stimulation/repression of their enzymatic systems. For example, in the laboratory, the lignin peroxidases of *P. chrysosporium* are induced under conditions of low nitrogen and repressed under conditions of high nitrogen (Fenn and Kirk, *Arch. Microbiol.*, vol. 130 (1981) pp. 59–65), but the lignolytic enzymes of other studied species of fungi are not regulated in this manner. Also, the ability of lignin-degrading fungi to degrade HAC's may not depend entirely on enzymes of the lignolytic system (Kohler et al., *Appl. Microbiol. Biotech.*, vol. 29 (1988) pp. 618–620), and under identical laboratory conditions, the lignolytic enzymes expressed by *P. chrysosporium* and *P. sordida* differ (R. Lamar, unpublished data). As this sparsity of data indicates, virtually nothing is known about how particular environmental and contamination site conditions influence the enzymatic pathways and/or growth of individual fungi, or how effectively or ineffectively the enzyme systems of different fungal species will function in degrading HAC's in uncontrolled field conditions. Consequently, the outcome of full scale field trials cannot be predicted.

Thus, the prior art teaches that lignin-degrading fungi can degrade HAC's in controlled laboratory experiments, and degrade PCP in soil in a controlled small scale field test. However, the prior art does not teach the methods or specific fungi required to successfully employ lignin-degrading fungi technology for use in the full scale bioremediation of halogenated hydrocarbon-contaminated, particularly PCP-contaminated soils and other materials.

SUMMARY OF THE INVENTION

The present invention provides a solid-phase bioremediation method utilizing naturally occurring fungi, with the capability to significantly reduce the concentration of a toxic contaminant in comparison to the concentration of the contaminant prior to treatment. The fungi in accordance with the present invention are not genetically altered or conditioned to specifically grow in the presence of a particular contaminant. Thus, the introduction of the fungi into the environment provides no new, nonnaturally-occurring organisms.

The method is particularly well suited for solid materials, such as, soils, sludge, sediments, and debris (e.g., woods), contaminated with halogenated hydrocarbons to provide a treated solid material of substantially reduced halogenated hydrocarbon content. The invention also encompasses a system for use of the method.

The method in accordance with the present invention includes inoculating a field-contaminated, nonsterile solid material having a halogenated hydrocarbon contaminant with an inoculum, and degrading the halogenated hydrocarbon contaminant to extractable and nonextractable degradation products. The method also suitably includes aerating and hydrating the solid material.

The inoculum contains a lignin-degrading fungal strain(s) and a lignocellulosic substrate. The lignin-degrading fungal strains are preferably selected from the genera Phanerochaete, Trametes, and Ceriporiopsis.

The halogenated hydrocarbon contaminant is preferably a single ring aromatic halogenated hydrocarbon, and the method is especially well suited to degrade pentachlorophenol (PCP).

The solid material of the present invention is a material that has been contaminated through functional use and is not artificially contaminated in the laboratory, or one that has been sterilized before further treatment in order to destroy other resistant bacteria and fungi. That is, the solid material is encountered, without any further changes before treatment, as a solid that has been contaminated in the field, a wood that has been contaminated in the field, a wood that has been intentionally treated for use in commerce, or a wood that is a contaminated by-product of industrial treatment.

In decontaminating a field-contaminated, nonsterile wood having halogenated hydrocarbon contaminants, the degradation process also includes mineralizing the organic carbon of the wood itself. A preferred fungal species for the degradation of wood is *Trametes hirsuta*.

The invention also encompasses a decontamination system for a contaminated solid material that is field-contaminated with a halogenated hydrocarbon. The system provides a treated solid material of substantially reduced contaminant concentration. The system includes an inoculum including a culture of a lignin-degrading fungal strain(s) for degrading halogenated hydrocarbons and a lignocellulosic substrate, and utilizes the method of the invention described herein.

The invention also encompasses a solid-phase bioremediation method comprising the steps of inoculating a field-contaminated, nonsterile solid material having a halogenated hydrocarbon contaminant with an inoculum, where the inoculum includes at least one lignin-degrading fungal strain and a lignocellulosic substrate; aeration and hydrating the solid material and degrading the halogenated hydrocarbon contaminant to nontoxic degradation products. The halogenated hydrocarbon contaminant is preferably a monocyclic ring aromatic halogenated hydrocarbon contaminant. The monocyclic aromatic halogenated hydrocarbon contaminant is most preferably pentachlorophenol. The solid material further includes an admixture of aromatic hydrocarbon contaminants. The method is well suited for the situation where the solid material is a soil. In addition, the method is suited for the solid material being debris and the situation where the debris is a wood. The lignin-degrading fungal strain is selected from the genera consisting of Phanerochaete, Trametes and Ceriporiopsis. Most preferably the lignin-degrading fungal strain is selected from the species *Phanerochaete chrysosporium, Phanerochaete sordida, Trametes hirsuta,* or *Ceriporiopsis subvermispora.*

The invention also includes a method for in-place bioremediation of a contaminated soil having halogenated hydrocarbon contaminants. The method includes the steps of inoculating in-place a field-contaminated, nonsterile soil having a halogenated hydrocarbon contaminant, with an inoculum including a lignocellulosic substrate and one or more lignin-degrading fungal species selected from the genera consisting of Phanerochaete and Trametes; aerating and hydrating the soil; and degrading the halogenated hydrocarbon contaminant to bioavailable degradation products. The method comprises using the fungal strains *Phanerochaete chrysosporium, Phanerochaete sordida* or *Trametes hirsuta*. The preferred lignin-degrading fungal strain for the soil is *Phanerochaete sordida*. The method is used for soils, including, clay soil, sandy soil, acidic soil, or sandy soil having a pH below 4. The lignocellulosic material preferably includes sawdust. The inoculum step provides an inoculum density in the soil of about 2 to 40% w/w. The soil may further contain halogenated hydrocarbon contaminants present in an admixture of aromatic hydrocarbons. Preferably the halogenated hydrocarbon contaminant is a monocyclic aromatic halogenated hydrocarbon. Most preferably the monocyclic aromatic halogenated hydrocarbon contaminant is pentachlorophenol having a concentration of between about 15 µg per g to about 1100 µg per g of soil. The method can be practiced where the pentachlorophenol concentration is between 400 µg per g to about 1100 µg per g of soil. A degradation product is pentachloroanisole. The method can be practiced where the degradation product is pentachloroanisole having a concentration of less than 10% of an initial pentachlorophenol concentration. The method is practiced wherein the aerating step includes tilling the soil approximately once per week.

The invention further comprises a method for decontaminating a field-contaminated wood having halogenated hydrocarbon contaminants, comprising the steps of inoculating a field-contaminated, nonsterile wood having a halogenated hydrocarbon contaminant, with an inoculum including a lignin-degrading fungal strain and a lignocellulosic substrate; aerating and hydrating the wood and degrading the halogenated hydrocarbon contaminant to nontoxic degradation products and at the same time mineralizing the wood. The method further is practiced with the degrading step being carried out for a reaction period of about 4 weeks and the wood having a dry weight loss of about 15% or more. The lignin-degrading fungal strain is selected from the genera consisting of Phanerochaete, Trametes and Ceriporiopsis. The lignin-degrading fungal strain is *Phanerochaete chrysosporium, Phanerochaete sordida, Trametes hirsuta,* or *Ceriporiopsis subvermispora*. The method preferably is practiced using the lignin-degrading fungus *Trametes hirsuta*.

The invention also comprises a decontamination system for a contaminated soil material comprising an inoculum including a culture of a lignin-degrading means for degrading halogenated hydrocarbons and a lignocellulosic substrate; inoculating means for inoculating a field-contaminated, nonsterile solid material, the solid material being soil or wood; aeration means for maintaining aerobic conditions in the solid material; hydrating means for maintaining moisture content in the solid material; and detection means for detecting the concentration of halogenated hydrocarbons. Lignin-degrading means includes means comprises a lignin-degrading fungal strain selected from the genera consisting of Phanerochaete, Trametes, and Cerioporiopsis. Preferably the lignin-degrading fungal strain is *Phanerochaete chrysosporium, Phanerochaete sordida, Trametes hirsuta,* or *Cerioporiopsis subvermispora*.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWINGS

The preferred exemplary embodiments of the present invention will hereinafter be described in conjunction with the appended drawing wherein like designations refer to like elements throughout and in which.

DETAILED DESCRIPTION

Figure 1:
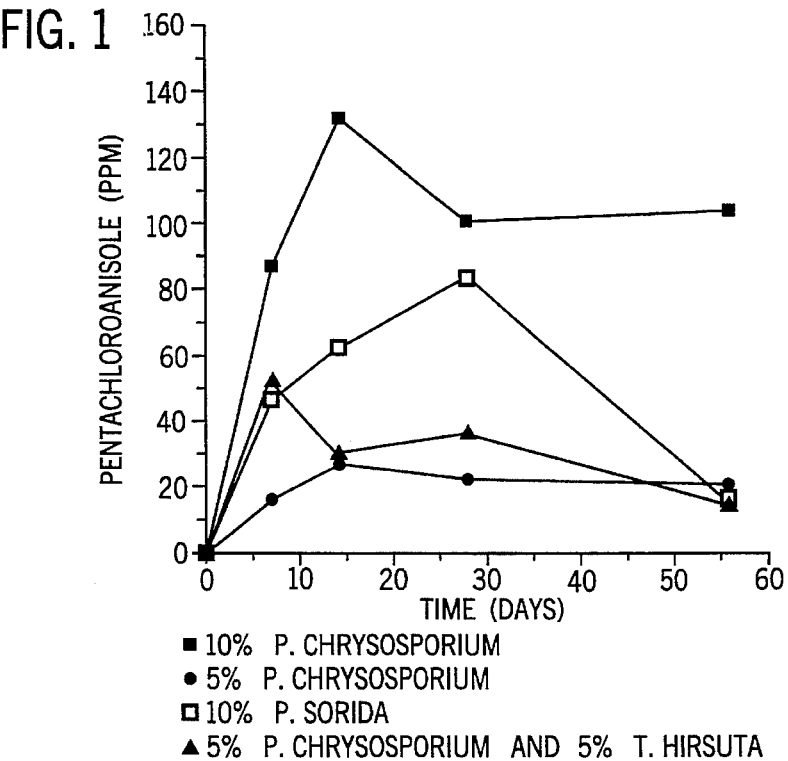
FIG. 1 is a graph of pentachloroanisole (PCA) concentration versus time in the Completely Random Design study of fungal action.

The present invention relates broadly to toxicology and environmental contamination. The present invention is particularly well suited for use in decontaminating of or disposal of solid materials contaminated with halogenated hydrocarbons.

The present invention is characterized by an ability to provide a treated contaminated solid material with a substantially reduced contaminant content both in the presence and absence of other chemical contaminants such as aromatic hydrocarbons. This ability is achieved by a novel combination of biochemical, chemical and physical features.

As used herein, the term "in situ" or "in place" is meant to refer to the site at which the contaminated solid material is found in the environment. The term "inoculum density" refers to the concentration of the fungal spores and/or fungal biomass introduced into the contaminated solid material in terms of per cent dry weight of the inoculum per dry weight of contaminated material. The term "lignocellulosic" in reference to certain types of substrates is meant to include lignosubstrates and cellulosic substrates as well as lignocellulosic substrates. The term "bioavailable" is meant to refer to the availability of a contaminant to a living organism and therefore the ability to be biochemically broken down by these organisms to degradation products.

The method in accordance with the present invention includes inoculating a field-contaminated, nonsterile solid material having a halogenated hydrocarbon contaminant with an inoculum, and degrading the halogenated hydrocarbon contaminant to less toxic degradation products. The method also suitably includes aerating and hydrating the solid material.

The inoculum contains a lignin-degrading fungal strain and a lignocellulosic substrate. The lignin-degrading fungi are preferably selected from the following genera: Phanerochaete, Trymetes, and Ceriporiopsis. The lignocellulosic substrate suitably includes sawdust. The contaminated material can optionally be supplemented with wood chips, preferably sterile aspen wood chips, before addition of the lignocellulosic substrate.

The halogenated hydrocarbon contaminant is preferably a single ring aromatic halogenated hydrocarbon, and the method is especially well suited to degrade pentachlorophenol (PCP). The halogenated hydrocarbon may be the only contaminant or one of many. It has been found that the lignin-degrading fungi of the present invention can degrade about 50% to about 90% of an initial or starting PCP concentration of between about 300 μg to about 1100 μg per g of solid material in about one to eight weeks at an inoculum density of about 2%–40% w/w.

The solid material is preferably a soil or debris, such as a wood, sludge, or any contaminated lignocellosic structure or sediment, which has been contaminated in the field (as opposed to treated with a contaminant in the laboratory); that is, the solid material of the present invention is a material that has been contaminated through functional use and is not artificially contaminated in the laboratory. The solid material is also not sterilized to remove other resident microorganisms or fungi.

The soil may range from a clay soil to a sandy soil. A clay soil is especially suitable, although sandy loams are also suitable. The pH of the soil may cover a broad range from acidic to basic. Soil that is acidic (pH $\leq 4$) is especially suitable, although neutral and alkaline soils are also suitable. The aeration of soil may be accomplished by periodically tilling the soil, approximately once per week; the moisture content is suitably maintained at about field capacity.

In decontaminating a field-contaminated, nonsterile wood having halogenated hydrocarbon contaminants, the degradation process also includes degrading the wood itself. The lignin-degrading fungi in accordance with the present invention can provide a dry weight loss in wood of 15% or more in about four weeks of reaction time; the preferred fungal strain is *Trametes hirsuta*.

The invention also encompasses a decontamination system for a contaminated solid material that is field contaminated with a halogenated hydrocarbon utilizing the method described herein. The system includes an inoculum including a culture of a lignin-degrading fungi for degrading halogenated hydrocarbons and a lignocellulosic substrate. The system also includes an inoculator or applicator for inoculating a field-contaminated, nonsterile solid material; an aerator for maintaining aerobic conditions in said solid material; a hydrating means for maintaining moisture content in said solid material; and also includes a detector for detecting the concentration of halogenated hydrocarbons so that the degree of decontamination can be ascertained.

The present invention is further explained by the following examples which should not be construed by way of limiting the scope of the present invention. In the following examples, organic solvent extracts of soil and chip samples were prepared by known methods and analyzed by gas chromatography. Pentachlorophenol was analyzed as the trimethylsilyl derivative using Sylon BTZ (Supelco Inc., Bellefonte, Pa.) as the derivatizing agent and quantitated using authentic derivatized standards. Pentachloroanisole was quantified with authentic standards. Analyses of extracts were performed on a Hewlett Packard Model 5890A or 5890II gas chromatograph equipped with $^{63}$Ni electron capture detectors, Model 7673A autosamplers, and split-splitless capillary column injection ports. Operating temperatures were: injector 220° C. and detector 300° C., carrier gas, He; and make-up gas, $N_2$. The columns were 30 m by 0.321 mm DB-5 fused silica capillary columns, film thickness 0.25 μm (J & W Scientific, Folsom, Calif.).

For analysis of data, an analysis of variance (ANOVA) was used at each sample time. If by ANOVA either CRD or BIB (as defined hereinbelow) treatments were shown to be significantly different, a Tukey multiple comparison test ($\alpha=0.05$) was performed to determine which treatments were different from others.

SOIL STUDIES

EXAMPLE 1

Fungi and Inocula Preparation

The fungi *P. chrysosporium*, *P. sordida*, *Ceriporiopsis subvermispora* (*C. subvermispora*), and *Trametes hirsuta* (*T. hirsuta*) were obtained from the culture collection of the Center for Forest Mycology Research (Forest Products Laboratory, Madison, Wis.). The fungi were grown and maintained on yeast malt peptone glucose (YMPG) agar slants (10 g/L glucose, 10 g/L malt extract, 2 g/L Bacto-Peptone, 2 g/L yeast extract, 1 g/L asparagine, 2 g/L monobasic potassium phosphate ($KH_2PO_4$), 1 g/L magnesium sulfate ($MgSO_4.7H_2O$), 1 g/L thiamine, and 23 g/L Bacto Agar). Fungal inocula described herein were prepared either by inoculating a sterile solid growth substrate of primarily lignocellulosic material (L. F. Lambert Spawn Co.) with the pure agar slant cultures (Examples 3 and 4 described hereinbelow) or by aseptically transferring pieces of fungal mycelium from the YMPG slants to 2% malt agar plates (100 mm by 20 mm) (Examples 5–9 described hereinbelow). The fungi were incubated until colony growth completely covered the plates. Fungal inoculum treatments are indicated by inoculum density in percentages (Examples 3 and 4), i.e., the percentage dry weight of the inoculum to the dry weight of the treated soil.

EXAMPLE 2

Soil Characteristics

Systematic sampling of an 18 m by 18 m level section of a waste sludge pile (former Brookhaven Wood Preserving facility, Brookhaven, Miss.) was conducted. Samples were taken to a depth of 30 cm along five rows that were 18 m long and 4.5 m apart. Ten samples were taken from each row at 1.8 m intervals. The soil samples were analyzed in duplicate for PCP, soil chemical characteristics, and volatile and semi-volatile organics.

The PCP concentration in the waste sludge pile ranged from 15 to 342 µg/g of soil. The soil chemical characteristics were: pH=3.8, cation exchange capacity 8.87 milliequivalents/100 g of soil, base saturation 54.8%, total nitrogen 0.04% and total carbon 2.17%. The soil was also found to contain small concentrations of volatile compounds and significant concentrations (approximately 2500 ppm total) of polyaromatic hydrocarbon components of creosote as indicated in Table 1 below.

TABLE 1

Concentrations[a] (mg/kg) of Volatile and
Semi-Volatile Organic Compounds
in Soil from the Waste Sludge Pile

| Compound | Concentration (mg/kg) |
|---|---|
| Volatiles | |
| 1,1,1-Trichloroethane | 0.057 |
| Toluene | 0.100 |
| Total xylenes | 0.950 |
| Semi-volatiles | |
| Pentachlorophenol | 51 |
| Napthalene | 250 |
| 2-Methylnapthalene | 95 |
| Acenapthylene | 6.4 |
| Acenapthene | 210 |
| Dibenzofuran | 110 |
| Fluorene | 170 |
| Phenanthrene | 470 |
| Anthracene | 110 |
| Fluoranthene | 290 |
| Pyrene | 270 |
| Benzo(a)anthracene | 55 |
| Chrysene | 59 |
| Benzo(b)fluoranthene | 43 |
| Benzo(k)fluoranthene | 43 |
| Benzo(a)pyrene | 21 |

[a]National Environmental Testing Method 8270

EXAMPLE 3

Fungi Decontamination in Completely Random Design (CRD) Plots

To analyze the ability of lignin-degrading fungi to degrade PCP in the soil of the waste sludge pile, an experimental plot section was constructed.

Soil was excavated from the upper 30 cm of the section of the waste sludge pile from which samples were initially taken for characterization. The excavated soil was sieved to exclude materials greater than 1.9 cm in diameter and replaced in plots as follows.

An 18 m by 24 m area with an approximate 3% slope along the short side was constructed using a sandy clay material. Three 3 m wide drainage swales with 10% slopes from outer edge to nadir were cut into the incline. Eleven 3 m by 3 m plot borders with 0.70 m high vertical side walls were constructed of #14 galvanized sheet metal. The plot borders were placed over the drainage swales and sunk into the sandy clay material so that the tops of the side walls were level. Each plot was lined with 4 mil polyethylene sheeting and drained using a perforated polyvinylchloride pipe placed on the liner in the middle of the V and connected to a drainage hose through a hole in the front wall of the plot. The drainage pipe was completely covered with gravel which was further covered with sand leaving approximately 45 cm to the top of the plot border. Each plot was then filled to a depth of 25 cm with sieved soil from the sludge pile.

Six treatments were evaluated in a completely random design (CRD). Six of the eleven 3 m by 3 m square plots were randomly assigned treatment with either *P. chrysosporium* (5%), *P. chrysosporium* (10%), *P. sordida* (10%), combination of *P. chrysosporium* (5%) and *T. hirsuta* (5%), lignocellulosic substrate (10%), or no amendments. On the day prior to application of the fungal inocula or standard substrate, the five plots receiving these treatments were amended with sterile aspen wood chips at a rate of 2.5% (w/w). Chips were sterilized three days before application and mixed into the soil to a depth of 20 cm with a rototiller. One day after chip application, the lignocellulosic substrate or fungal inocula was mixed into the soil to a depth of 20 cm with a rototiller. During treatment application, the soil in each of the CRD plots was physically divided into four 1.5 m by 1.5 m sections. These sections were then treated as replications during maintenance and sampling.

Soil water content was determined daily and maintained at a minimum of 20% by the application of tap water when necessary. Additionally, the soil in each plot was mixed once a week by tilling and manual shoveling to provide aeration.

Soil samples were taken with a core sampler to a depth of 20 cm. The soil samples were collected in triplicate from each section 1, 7, 14, 28, and 56 days after application of the fungal inocula or standard substrate. Samples were analyzed for PCP and pentachloroanisole (PCA) concentration.

The results of the study are shown in Table 2.

TABLE 2

Effect of CRD Treatments on the Percentage of PCP
Remaining in Soil Over Time[a]

| Treatment[c] | PCP remaining (%) at various days after treatment[b] | | | |
|---|---|---|---|---|
| | 7 | 14 | 28 | 56 |
| *P. chrysosporium* (5%) | 49a | 63a | 63ab | 85c |
| *P. chrysosporium* (10%) | 52a | 65a | 62a | 33ab |
| *P. sordida* (10%) | 58a | 47a | 50a | 11a |
| *P. chrysosporium* (5%) and *T. hirsuta* (5%) | 37a | 51a | 62a | 77bc |
| Standard Substrate (10%) | 118c | 79b | 98bc | 86c |
| No amendments | 93b | 97b | 106c | 85c |
| P[d] | 0.0001 | 0.0105 | 0.0004 | 0.0001 |

[a]If the ANOVA showed a significant difference among treatment means, Tukey's multiple comparison test was used to determine treatment differences.
[b]Treatment means within a column followed by the same letter are not significantly different ($\alpha = 0.05$).
[c]Soils in all treatments, except the no amendment treatment, were amended with wood chips at a rate of 2.5%.
[d]P equals the probability of a larger F value for difference among treatment means.

Compared to the PCP concentrations on day 1, which ranged from 500–1000 µg/g, all of the fungal inoculum treatments resulted in substantial decreases in the PCP levels by 7 days post amendment. These decreases ranged from a high of 63% in the plots treated with *P. chrysosporium* (5%) and *T. hirsuta* (5%) to a low of 42% in the plots treated with *P. sordida* (10%). The PCP level then remained fairly stable through 28 days in all of the fungal treatments. By 56 days however, the PCP concentration in the plots treated with either *P. chrysosporium* (10%) or *P. sordida* (10%) had decreased substantially further giving 67% and 89% depletion, respectively, at the end of the test period. It is noted that the two other fungal treatments (*P. chrysosporium* (5%) and *P. chrysosporium* (5%)/*T. hirsuta* (5%)) had final PCP concentrations higher than those at days 7, 14, and 28. This was presumed to be due to incorporation of fresh PCP from nontreated soil, introduced into the upper 20 cm layer during the periodic tilling, and that the biomass of the fungal inoculum was not sufficient to metabolize. In comparison, the two control plots, one of which was nonamended and the other amended with lignocellulosic substrate alone, showed no significant decrease in PCP concentrations over the 56-day period.

The accumulation of PCA, a less toxic methylated derivative of PCP (Ruckdeschel and Renner, *Appl. Environ. Microbiol.*, vol. 53 (1986) pp. 2689–2692), in soils inoculated with *P. chrysosporium* or *P. sordida* has been observed, therefore, soil samples from the plots treated with fungi were also analyzed for PCA. PCA was not detected in initial soil samples or at any time in samples taken from the nonamended plot. However, PCA accumulated in all fungal treated plots. As shown in FIG. 1, the increases were maximal by 14 to 28 days after which they either stabilized or decreased. The largest increase was seen in the plot treated with *P. chrysosporium* (10%); the smallest were in the plots treated with *P. chrysosporium* (5%) alone or in combination with *T. hirsuta* (5%) (FIG. 1). In the case of the plots treated with *P. sordida* (10%), although PCA did accumulate to levels almost as high as that seen in the plots treated with *P. chrysosporium* (10%), unlike *P. chrysosporium*, it was apparently able to metabolize the PCA further such that the final level of PCA was comparable to that seen in the plot treated with *P. chrysosporium* (5%) (FIG. 1).

EXAMPLE 4

Balanced Incomplete Block (BIB) Design Plots

Five treatments were evaluated in a balanced incomplete block design (BIB). The remaining five 3 m by 3 m plots constructed as described in Example 3 (hereinafter referred to as blocks), were divided into four 1.5 m by 1.5 m squares. Each treatment was randomly assigned to four one square sections in the five blocks. Thus, each treatment was replicated four times. The treatments were either *P. chrysosporium* (10%), *P. chrysosporium* (13%), *P. chrysosporium* (10%, day 0 with 3% added at day 14), *T. hirsuta* (10%), or chips alone (2.5%).

Application of the treatments, sampling of the soil, and care and maintenance of the plots were as described in Example 3.

The results of the study are shown in Table 3.

TABLE 3

Effect of BIB Treatments on the Percentage of PCP Remaining in soil Over Time[a]

| Treatment[c] | PCP remaining (%) at various days after treatment[b] | | | |
|---|---|---|---|---|
| | 7 | 14 | 28[d] | 56 |
| *P. chrysosporium* (10%) | 58a | 45a | 37a | 28a |
| *P. chrysosporium* (13%) | 87a | 72a | 92ab | 48a |
| *P. chrysosporium* (10%, day 0) (3%, day 14) | 81a | 103a | 57a | 45a |
| *T. hirsuta* (10%) | 101a | 102a | 86ab | 45a |
| Chips only (2.5%) | 103a | 102a | 136b | 114b |
| P[e] | 0.3017 | 0.1547 | 0.0604 | 0.0051 |

[a]If the ANOVA showed a significant difference among treatment means, Tukey's multiple comparison test was used to determine treatment differences.
[b]Treatment means within a column followed by the same letter are not significantly different ($\alpha = 0.05$).
[c]Soils in all treatments were amended with wood chips at a rate of 2.5%.
[d]The F-test generated by the ANOVA for sample 6 (day 28) had a significance level of 0.0604. Therefore, Tukey's test was performed unprotected.
[e]P equals the probability of a larger F value for difference among treatment means.

All of the treatments with *P. chrysosporium* resulted in decreases in the concentration of PCP by 7 days, and although there was some variability, the levels of PCP then gradually declined further through the 56 days. The final percent of PCP decreases for treatment with *P. chrysosporium* (10%), *P. chrysosporium* (13%), and *P. chrysosporium* (10%, day 0; 3% day 14) were 72%, 52%, and 55%, respectively. Treatment with *T. hirsuta* (10%) also caused decreases in the PCP concentration, however, there was a lag time. No decrease was observed at 7 or 14 days, but by 26 days PCP levels had been decreased 14%, and by 56 days the decrease had increased to 55%. In contrast, no decrease in PCP levels was obtained in the squares amended with chips alone. These results, along with those of Example 3, clearly show the ability of lignin-degrading fungi to degrade PCP under conditions of high contaminant concentrations and mixed contaminant conditions.

Figure 2:
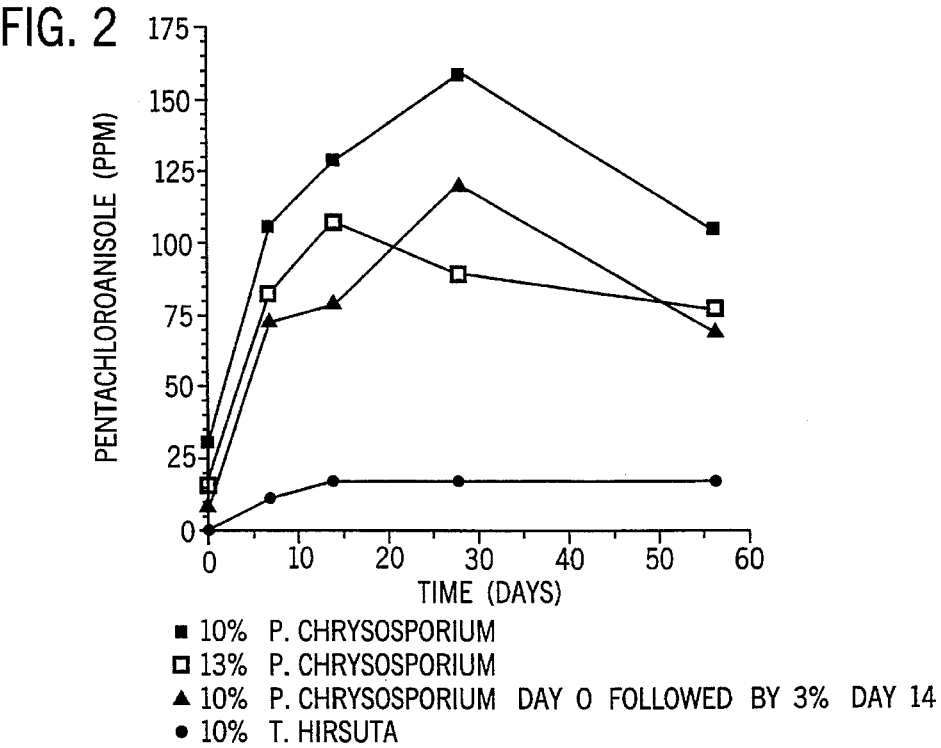
FIG. 2 is a graph of PCA concentration versus time in the Balanced Incomplete Block study of fungal action.

Analysis of the PCA level in these squares in shown in FIG. 2. All of the squares treated with *P. chrysosporium* showed increases in PCA which maximized at 14 to 28 days and then only decreased slightly. This agrees with the data in Example 3 where it appeared that *P. chrysosporium* was not able to metabolize PCA at any appreciable rate under these conditions. In contrast, the squares treated with *T. hirsuta* showed very little accumulation of PCA (FIG. 2).

WOOD STUDIES

EXAMPLE 5

Contaminated Wood Preparation

To analyze the ability of lignin-degrading fungi to degrade PCP in contaminated wood, six PCP-treated ammunition boxes were obtained for study. The boxes were variously constructed of lodgepole (*Pinus contorta* Dougl. ex Loud), ponderosa pine (*Pinus ponderosa* Dougl. ex Loud), yellow poplar (*Liriodendron tulipifera* L.), all softwoods, and the hardwoods blackgum (*Nyssa sylvatica* Marsh.) and sweetgum (*Liquidambar styraciflua* L.). The boxes were disassembled and the hardwood and softwood materials separated. The materials were chipped using a hammer to pass a 3.8 cm screen. Sterile chips were prepared by adjusting the moisture content of the chips to 60% with distilled water and autoclaving at 121° C. for 30 min. on 3 successive days.

EXAMPLE 6

Effects of wood type, chip sterilization, and fungal species (*P. chrysosporium* and *P. sordida*) on PCP decontamination In this experiment, the effects of wood type, chip sterilization and fungal species on concentrations of PCP in wood chips were evaluated. Chip cultures were prepared by aseptically placing approximately 10 g of either sterile or nonsterile softwood or hardwood chips in a sterile aluminum foil-covered Erlenmeyer flask. Approximately half of the agar from an inoculum plate of *P. chrysosporium* or *P. sordida* (see, Example 1) was then aseptically added to the flask along with 5000 ppm glutamine. Noninoculated control cultures were also set up. There were five cultures per treatment. Cultures were incubated at 30° C. Initial concentrations of PCP and PCA were determined on 10 replicate samples from each batch of sterile or nonsterile wood chips. Concentrations of PCP and PCA were determined at 1, 2, 4, and 6 weeks post inoculation by gas chromatography of organic solvent extracts. Analyses were performed in duplicate at each sample time and the results are given in Table 4 below.

TABLE 4

Initial Concentrations of PCP in Autoclaved and Nonautoclaved Hardwood and Softwood Chips

| Wood Type | PCP ($\mu g\ g^{-1}$) | | |
|---|---|---|---|
| | Autoclaved | Nonautoclaved | Mean |
| Hardwood | 281.7 | 355.8 | 338.7 |
| Softwood | 233.7 | 428.5 | 379.8 |
| Mean | 257.7 | 390.2 | |

As shown in Table 4, the initial concentrations of PCP in the chips was affected by autoclaving; the concentration was higher in nonautoclaved than in autoclaved chips in both wood types.

Figure 3A:
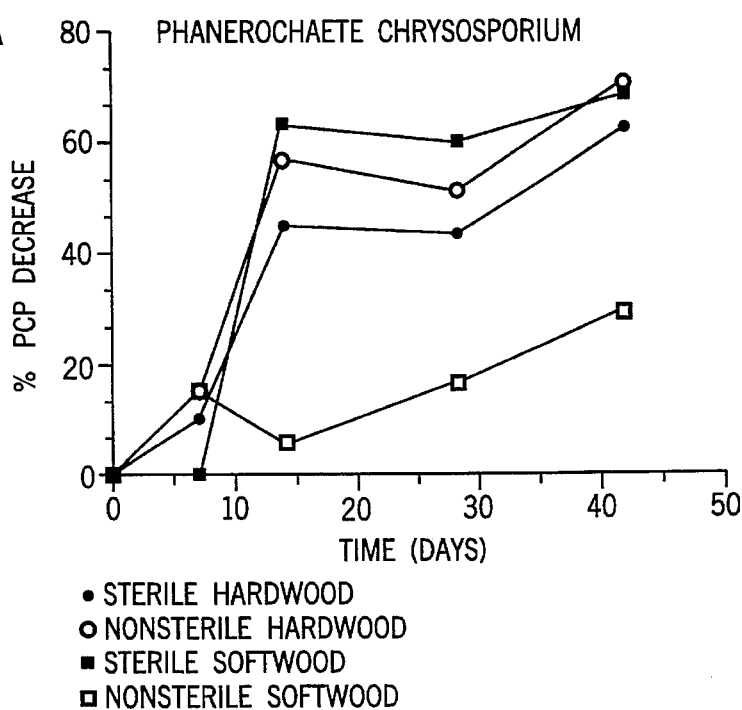
FIG. 3A is a graph of the percent decrease in PCP concentration versus time for *Phanerochaete chrysosporium* fungal action on various woods.
Figure 3B:
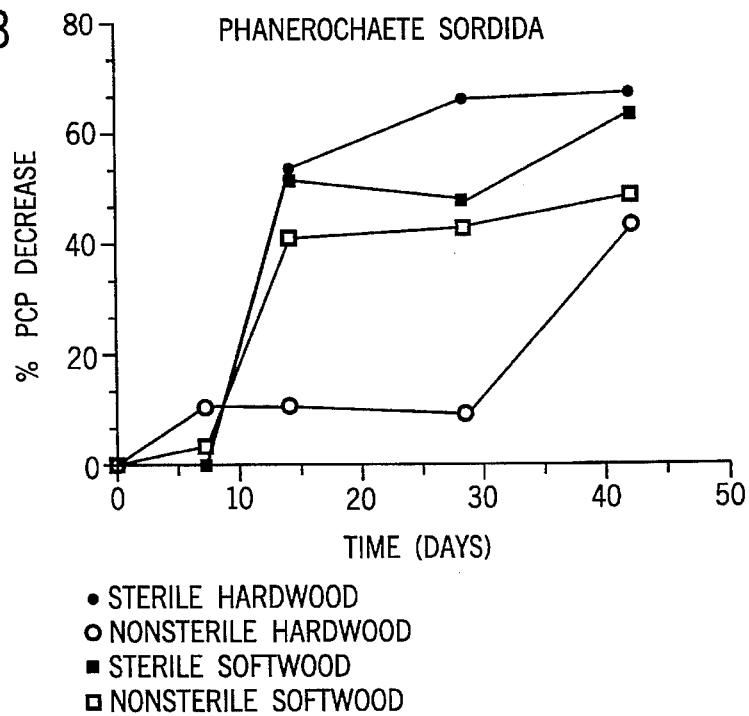
FIG. 3B is a graph of the percent decrease in PCP concentration versus time for *Phanerochaete sordida* fungal action on various woods.

As best seen in FIGS. 3A and 3B, inoculation of sterile and nonsterile, softwood or hardwood chips with either *P. chrysosporium* or *P. sordida* resulted in decreases in the PCP concentration in the chips after 6 weeks. As shown in FIG. 3A, in chip cultures inoculated with *P. chrysosporium*, decreases in the PCP concentration in sterile and nonsterile hardwood and sterile softwood were rapid and extensive between days 7 and 14 post inoculation and reached a maximum measured decrease of 63–72% by 42 days. In nonsterile softwood, *P. chrysosporium* did not give as large or as rapid an effect, with the decrease in PCP rising slowly to reach 30% after 42 days. As shown in FIG. 3B, in chip cultures inoculated with *P. sordida*, decreases in the PCP concentrations in sterile and nonsterile softwood and sterile hardwood also mostly occurred during days 7–14, with the final decreases reaching from 50–66%. In nonsterile hardwood, significant decreases in the PCP concentration did not occur until the period between days 28–42 by the end of which PCP concentrations were decreased 45%. No decreases in PCP concentrations were observed in either sterile or nonsterile noninoculated chips, indicating that the observed PCP decreases were due to the activities of the inoculated fungi.

Figure 4A:
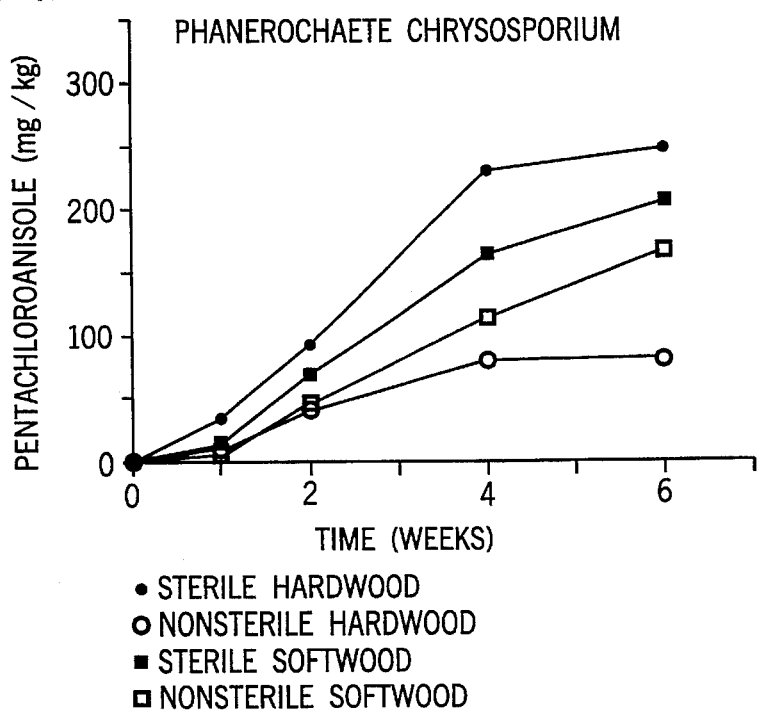
FIG. 4A is a graph of the accumulation of PCA versus time for *Phanerochaete chrysosporium* fungal action in various woods.
Figure 4B:
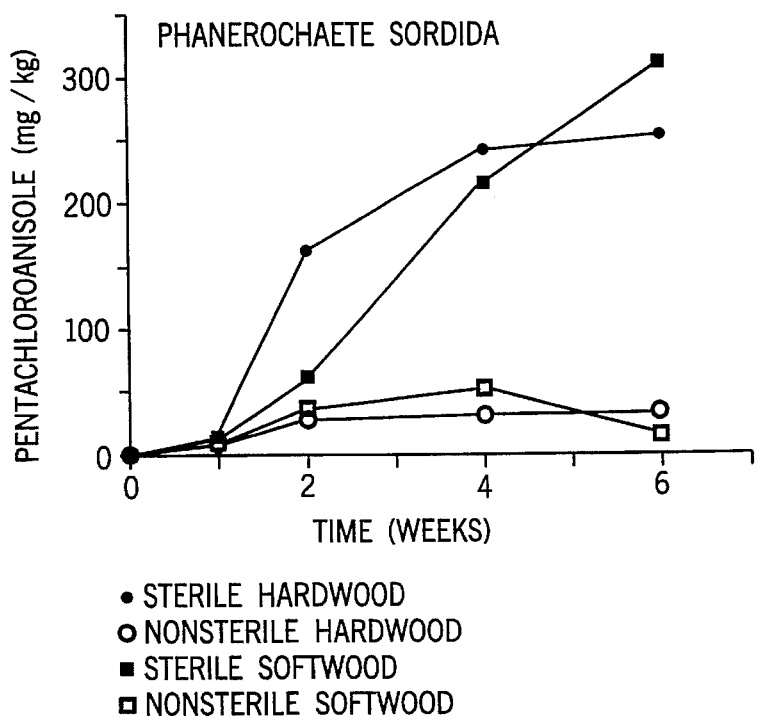
FIG. 4B is a graph of the accumulation of PCA versus time for *Phanerochaete sordida* action in various woods.

As seen in FIGS. 4A and 4B, the depletion of PCP was always accompanied by formation of PCA. However, no accumulation of PCA was observed in noninoculated cultures, indicating that accumulation in inoculated chips was due to the activity of the fungi. Accumulation of PCA in sterile cultures was greater than in nonsterile cultures of both fungi, but particularly those inoculated with *P. sordida*, as shown in FIG. 4B. However, it should be noted that the lowest PCP decreases were also associated with *P. sordida* inoculation of nonsterile hardwood and softwood. Also, in nonsterile hardwood and softwood chips inoculated with *P. chrysosporium*, 65% and 72%, respectively, of the PCP decrease was due to conversion of PCP to PCA. In sterile chips inoculated with either fungus, virtually all of the PCP decrease was due to conversion to PCA.

EXAMPLE 7

Effect of carbon and nitrogen supplementation on PCP decontamination using *P. chrysosporium*

A study was conducted to ascertain the effects of different carbon and nitrogen source supplementation on the concentrations of PCP and PCA in softwood chips inoculated with *P. chrysosporium*. Chip cultures were set up as described in Example 6 except each culture was supplemented with either glucose (5.1 g/g of chips), glycerin (5.3 g/g), ammonium chloride ($NH_4Cl$) (3.7 g/g), glutamine (5 g/g), or potassium nitrate ($KNO_3$) (2.5 g/g). Control cultures with no supplementation were also set up. Three inoculated and two noninoculated cultures were prepared for each treatment. Concentrations of PCP and PCA were determined on duplicate samples from each culture after 3 weeks.

Figure 5:
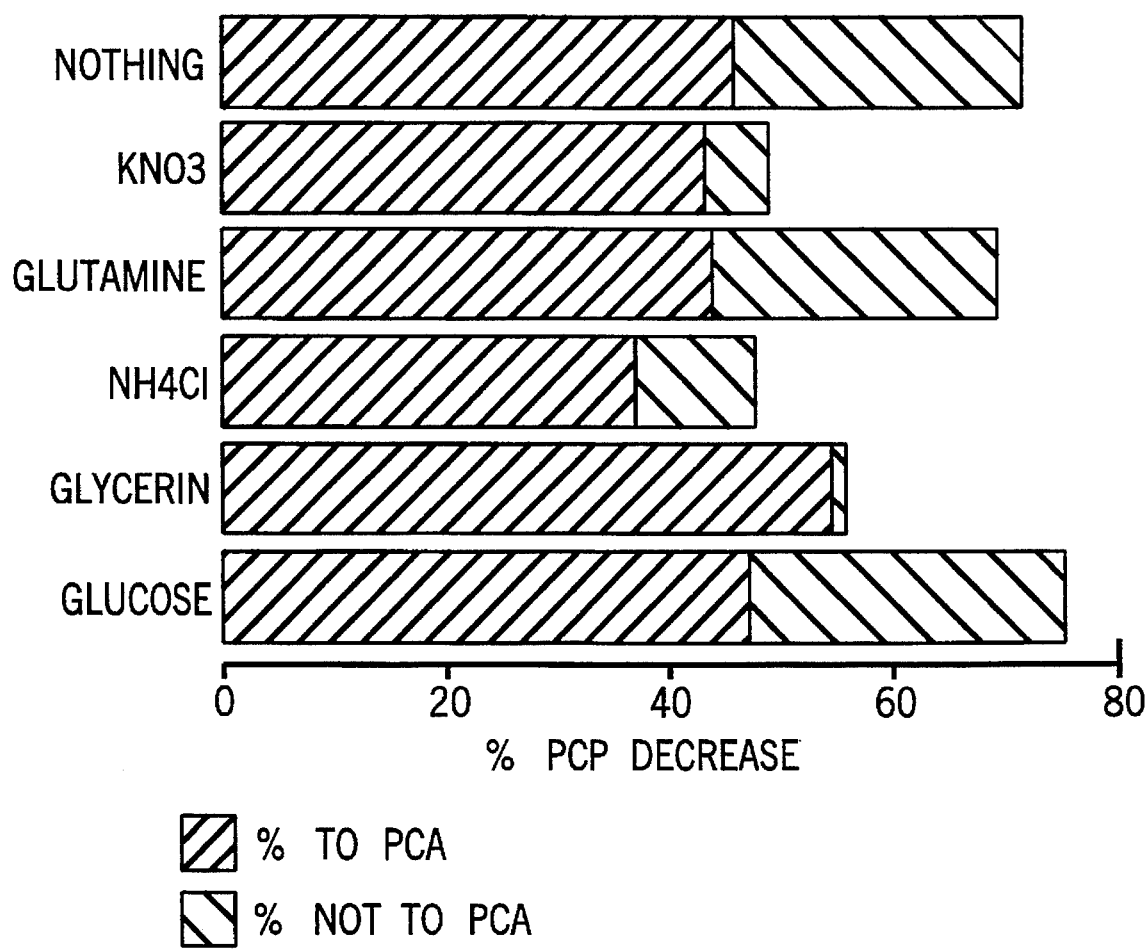
FIG. 5 is a bar graph showing the percentage PCP decrease after 3 weeks in PCP-contaminated softwood chips supplemented with different sources of nitrogen and/or carbon and inoculated with *P. chrysosporium*.

As seen in FIG. 5, there was a decrease in the PCP concentration in inoculated chips regardless of supplement treatment. The largest decreases were seen with glucose, glutamine and no supplement, averaging around 70%. Again, these decreases were always accompanied by increases in PCA concentration. However, the percentage of the total decrease in the PCP concentrations as a result of PCA formation varied greatly among the treatments. When chips were supplemented with glycerin, virtually all of the PCP decrease was due to conversion to PCA. In chips receiving inorganic sources of nitrogen, the majority of the PCP loss (77–89%) was due to conversion of PCP to PCA. Finally, in chips supplemented with glucose or glutamine and in chips receiving no supplement, slightly less than two-thirds (61–63%) of the PCP decrease was due to conversion to PCA.

EXAMPLE 8

Ability of *T. hirsuta* and *C. subvermispora* to degrade PCP

The ability of *T. hirsuta* or *C. subvermispora* to deplete PCP in sterile softwood chips was evaluated. Chip cultures were set up as described in Example 6 except that the fungi used for inoculation were *T. hirsuta* or *C. subvermispora*. Six cultures were set up for each treatment. Initial concentrations of PCP and PCA were determined on 10 replicate samples for each batch of chips. Concentrations of PCP and PCA were determined after 2 and 4 weeks of incubation on replicate samples and the results are given in Tables 5 and 6 below.

TABLE 5

Concentrations of PCP and PCA in
Sterile Softwood Chips Inoculated With
*Trametes Hirsuta* or Left Noninoculated[a]

| | PCP (µg g$^{-1}$) | | | PCA (µg g$^{-1}$) | | |
|---|---|---|---|---|---|---|
| | Day | | | | | |
| Fungus | 0 | 14 | 28 | 0 | 14 | 28 |
| T. hirsuta | 381.7a | 241.0b | 145.4c | 2.8a | 2.3a | 4.4c |
| Noninoculated | 381.7a | 353.3a | 355.5a | 2.8a | 1.8ab | 1.3b |

[a]Means followed by the same letter are not significantly different according to Scheffe's test ($\alpha = 0.05$).

TABLE 6

Concentrations of PCP and PCA in
Sterile Softwood Chips Inoculated With
*Ceriposiopsis Subvermispora* or Left Noninoculated[a]

| | PCP (µg g$^{-1}$) | | | PCA (µg g$^{-1}$) | | |
|---|---|---|---|---|---|---|
| | Day | | | | | |
| Fungus | 0 | 14 | 28 | 0 | 14 | 28 |
| C. subvermispora | 448.0a | 300.0b | 266.1c | 5.1a | 4.4a | 6.2a |
| Noninoculated | 448.0a | 408.9a | 418.9a | 5.1a | 4.1a | 3.6a |

[a]Means within compound followed by the same letter are not significantly different according to Scheffe's test ($\alpha = 0.05$).

As seen from the results in Table 5, inoculation of the sterile PCP-contaminated softwood chips with *T. hirsuta* resulted in the PCP concentration decreasing from 382 µg/g to 145 µg/g by the end of the four week incubation period. This represented a 62% decrease in the amount of PCP which is similar in magnitude to that removed by *P. chrysosporium* and *P. sordida* in Example 5. However, the decrease affected by *T. hirsuta* was not due to transformation to and accumulation of PCA as it was in chips inoculated with *P. chrysosporium* or *P. sordida*.

As seen in Table 6, inoculation of PCP-contaminated softwood chips with *C. subvermispora* resulted in a decrease in the concentration of PCP from 448 µg/g to 266 µg/g after 4 weeks. This 37% decrease was the least of any of the fungi evaluated. However, as was observed with *T. hirsuta*, this decrease was not due to accumulation of PCA.

EXAMPLE 9

Ability of the four fungal strains to effect dry weight loss of wood

The ability of the different fungal strains to effect dry weight loss was also evaluated. Chip cultures were set up as described in Example 6 using sterile softwood chips inoculated with one of the four fungal strains. After 4 or 9 weeks, dry weight loss was determined by removing mycelium from the chip surfaces, drying the chips at 105° for 24 hours, and comparing the weight to the preincubation dry weight. The results are given in Table 7 below.

TABLE 7

Percentage Dry Weight Loss of
Sterile Softwood Chips 4 or 9 Weeks After
Inoculation With *P. chrysosporium, P. sordida,
T. hirsuta* or *C. subvermispora*

| FUNGUS | TIME | WEIGHT LOSS (%) |
|---|---|---|
| P. chrysosporium | (9 weeks) | 18 |
| P. sordida | (9 weeks) | 14.9 |
| Noninoculated | (9 weeks) | 0.1 |
| T. hirsuta | (4 weeks) | 24.5 |
| C. subvermispora | (4 weeks) | 17.4 |
| Noninoculated | (4 weeks) | 1.6 |

Results in Table 7 show that inoculation of softwood chips with *T. hirsuta* resulted in a 25% weight. loss after 4 weeks. This weight loss was much greater than the 18% and 15% decreases obtained from inoculation with *P. chrysosporium* or *P. sordida*, respectively, after 9 weeks. After 4 weeks, *C. subvermispora* decreased the dry weight of the PCP-contaminated softwood chips by 17%. This loss was greater than those obtained form inoculation with *P. chrysosporium* or *P. sordida* but less than that obtained with *T. hirsuta*. No weight loss was observed in noninoculated chips.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A method for in-place bioremediation of a contaminated soil having halogenated hydrocarbon contaminants, comprising the steps of:

inoculating in place a field-contaminated, nonsterile soil having pentachlorophenol contaminant, with an inoculum including a lignocellulosic substrate and the lignin-degrading fungal species *Phanerochaete sordida*, said lignocellulosic substrate in an amount sufficient to produce a biomass of said inoculum sufficient to metabolize said pentachlorophenol contaminant;

aerating and hydrating said inoculated soil for a time and under conditions sufficient for said inoculum to metabolize said pentachlorophenol contaminant under ambient temperature conditions; and degrading said pentachlorophenol contaminant by said inoculum to bioavailable degradation products.

2. A method for in-place bioremediation of a contaminated soil having halogenated hydrocarbon contaminants, comprising the steps of:

inoculating in place a field-contaminated, nonsterile soil having pentachlorophenol contaminant, with an inoculum including a lignocellulosic substrate and one or more lignin-degrading fungal strains of species selected from the group consisting of *Phanerochaete chrysosporium, Phanerochaete sordida*, and *Trametes hirsuta*, said lignocellulosic substrate in an amount sufficient to produce a biomass of said inoculum sufficient to metabolize said pentachlorophenol contaminant;

aerating and hydrating said inoculated soil for a time and under conditions sufficient for said inoculum to metabolize said pentachlorophenol contaminant under ambient temperature conditions; and degrading said pentachlorophenol contaminant by said inoculum to bioavailable degradation products, wherein said inoculating step provides an inoculum density in said soil of about 2–40% w/w of a dry weight of said inoculum to a dry weight of said inoculated soil.

3. A method for in-place bioremediation of a contaminated soil having halogenated hydrocarbon contaminants, comprising the steps of:

inoculating in place a field-contaminated, nonsterile soil having pentachlorophenol contaminant, with an inoculum including a lignocellulosic substrate and one or more lignin-degrading fungal strains of species selected from the group consisting of *Phanerochaete chrysosporium*, *Phanerochaete sordida*, and *Trametes hirsuta*, said lignocellulosic substrate in an amount sufficient to produce a biomass of said inoculum sufficient to metabolize said pentachlorophenol contaminant;

aerating and hydrating said inoculated soil for a time and under conditions sufficient for said inoculum to metabolize said pentachlorophenol contaminant under ambient temperature conditions; and degrading said pentachlorophenol contaminant by said inoculum to bioavailable degradation products, wherein said pentachlorophenol contaminant has a concentration of between about 15 µg per g to about 1100 µg per g soil, prior to inoculating the soil.

4. A method for in-place bioremediation of a contaminated soil having halogenated hydrocarbon contaminants, comprising the steps of:

inoculating in place a field-contaminated, nonsterile soil having pentachlorophenol contaminant, with an inoculum including a lignocellulosic substrate and the lignin-degrading fungal species of *Phanerochaete sordida*, said lignocellulosic substrate in an amount sufficient to produce a biomass of said inoculum sufficient to metabolize said pentachlorophenol contaminant;

aerating and hydrating said inoculated soil for a time and under conditions sufficient for said inoculum to metabolize said pentachlorophenol contaminant under ambient temperature conditions; and degrading said pentachlorophenol contaminant by said inoculum to bioavailable degradation products, wherein said pentachlorophenol contaminant has a concentration of between about 400 µg per g to about 1100 µg per g of soil, prior to inoculating the soil.

5. A method for in-place bioremediation of a contaminated soil having halogenated hydrocarbon contaminants, comprising the steps of:

inoculating in place a field-contaminated, nonsterile soil having pentachlorophenol contaminant, with an inoculum including a lignocellulosic substrate and one or more lignin-degrading fungal strains of species selected from the group consisting of *Phanerochaete chrysosporium*, *Phanerochaete sordida*, and *Trametes hirsuta*, said lignocellulosic substrate in an amount sufficient to produce a biomass of said inoculum sufficient to metabolize said pentachlorophenol contaminant;

aerating and hydrating said inoculated soil for a time and under conditions sufficient for said inoculum to metabolize said pentachlorophenol contaminant under ambient temperature conditions; and degrading said pentachlorophenol contaminant by said inoculum to bioavailable degradation products, wherein a degradation product is pentachloroanisole.

6. The method of claim 5, wherein said soil is a clay soil.

7. The method of claim 5, wherein said soil is sandy.

8. The method of claim 5, wherein said soil has a pH below 4.

9. The method of claim 5, wherein said soil is acidic.

10. The method of claim 5, wherein said lignocellulosic substrate includes sawdust.

11. The method of claim 5, wherein said pentachlorophenol contaminant is present in an admixture of aromatic hydrocarbons.

12. A method for in-place bioremediation of a contaminated soil having halogenated hydrocarbon contaminants, comprising the steps of:

inoculating in place a field-contaminated, nonsterile soil having pentachlorophenol contaminant, with an inoculum including a lignocellulosic substrate and one or more lignin-degrading fungal strains of species selected from the group consisting of *Phanerochaete chrysosporium*, *Phanerochaete sordida*, and *Trametes hirsuta*, said lignocellulosic substrate in an amount sufficient to produce a biomass of said inoculum sufficient to metabolize said pentachlorophenol contaminant;

aerating and hydrating said inoculated soil for a time and under conditions sufficient for said inoculum to metabolize said pentachlorophenol contaminant under ambient temperature conditions; and degrading said pentachlorophenol contaminant by said inoculum to bioavailable degradation products, wherein said pentachlorophenol has an initial concentration prior to degradation and wherein a degradation product is pentachloroanisole having a concentration of less than 10% of said initial concentration of said pentachlorophenol.

13. A method for in-place bioremediation of a contaminated soil having halogenated hydrocarbon contaminants, comprising the steps of:

inoculating in place a field-contaminated, nonsterile soil having pentachlorophenol contaminant, with an inoculum including a lignocellulosic substrate and one or more lignin-degrading fungal strains of species selected from the group consisting of *Phanerochaete chrysosporium*, *Phanerochaete sordida*, and *Trametes hirsuta*, said lignocellulosic substrate in an amount sufficient to produce a biomass of said inoculum sufficient to metabolize said pentachlorophenol contaminant;

aerating and hydrating said inoculated soil for a time and under conditions sufficient for said inoculum to metabolize said pentachlorophenol contaminant under ambient temperature conditions, said aerating step including tilling said soil approximately once per week; and degrading said pentachlorophenol contaminant by said inoculum to bioavailable degradation products.

* * * * *